United States Patent [19]

Someya et al.

[11] Patent Number: 4,746,359
[45] Date of Patent: May 24, 1988

[54] HYDROXYACETIC ACID AMIDE DERIVATIVES, AND HERBICIDAL COMPOSITIONS CONTAINING THEM

[75] Inventors: Shinzo Someya, Tokorozawa; Seigo Koura, Tokyo; Mikio Ito, Tokuyama; Akira Nakanishi, Yokohama; Yuji Nonaka, Tokuyama, all of Japan

[73] Assignees: Toyo Soda Manufacturing Co., Ltd., Yamaguchi; Agro-Kanesho Co., Ltd., Tokyo, both of Japan

[21] Appl. No.: 48,757

[22] Filed: May 12, 1987

[30] Foreign Application Priority Data

May 21, 1986 [JP] Japan ................... 61-116344

[51] Int. Cl.⁴ .................. A01N 43/40; C07D 213/64
[52] U.S. Cl. ........................................ 71/94; 546/291
[58] Field of Search ................... 546/291; 71/94

[56] References Cited

U.S. PATENT DOCUMENTS

| 3,954,442 | 5/1976 | Becker et al. | 546/291 |
| 4,238,626 | 12/1980 | Nahm et al. | 546/291 |
| 4,391,995 | 7/1983 | Nahm et al. | 546/291 |
| 4,589,907 | 5/1986 | Felix | 546/291 |

FOREIGN PATENT DOCUMENTS

| 1599121 | 7/1977 | United Kingdom | 546/291 |
| 1599126 | 7/1977 | United Kingdom | 546/291 |
| 2015995 | 3/1979 | United Kingdom | 546/291 |

Primary Examiner—Alan L. Rotman
Assistant Examiner—J. Richter
Attorney, Agent, or Firm—Nixon & Vanderhye

[57] ABSTRACT

A hydroxyacetic acid amide derivative having the formula:

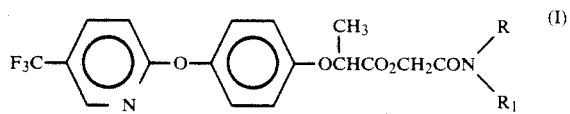

wherein each of R and $R_1$ which may be the same or different, is an alkyl, alkenyl, alkynyl or alkoxyalkyl group having from 1 to 4 carbon atoms, provided that R and $R_1$ are not simultaneously alkyl groups.

6 Claims, No Drawings

HYDROXYACETIC ACID AMIDE DERIVATIVES, AND HERBICIDAL COMPOSITIONS CONTAINING THEM

The present invention relates to novel hydroxyacetic acid amide derivatives, processes for their production, and novel selective herbicidal compositions containing them has active ingredients.

A number of hydroxyacetic acid amide derivatives having herbicidal activities have been known. However, the activities of such conventional substances are not necessarily adequate as will be described hereinafter.

There is a strong demand in the market for a selective herbicide which is capable of killing gramineous weeds by either soil treatment or foliage treatment without presenting an adverse effect to crop plants in the cultivation of paddy rice plants or broad leaf crop plants in spite of the fact a number of herbicides including the above-mentioned conventional hydroxyacetic acid amide derivatives have been developed and marketed.

It is an object of the present invention to provide an improved selective herbicide which satisifies the demand in the market.

As a result of extensive research to obtain an effective selective herbicide, the present inventors have found that a certain specific hydroxyacetic amide derivative satisfies the object, and the present invention has been accomplished on the basis of this discovery.

The present invention provides a novel hydroxyacetic amide derivative having the formula:

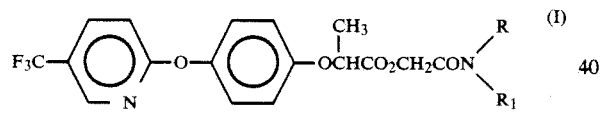

wherein each of R and $R_1$ which may be the same or different, is an alkyl, alkenyl, alkynyl or alkoxyalkyl group having from 1 to 4 carbon atoms, provided that R and $R_1$ are not simultaneously alkyl groups.

The compound of the formula I of the present invention can readily be prepared by a process which comprises reacting a compound of the formula:

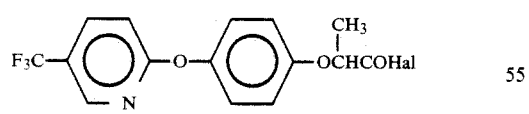

wherein Hal is a halogen atom, with a compound of the formula:

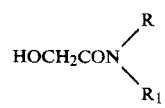

wherein R and $R_1$ are as defined above, or a process which comprises reacting a compound of the formula:

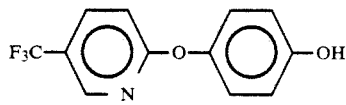

with a compound of the formula:

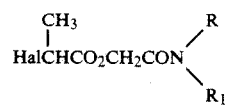

wherein R and $R_1$ are as defined above, and Hal is a halogen atom.

The present invention also provides a herbicidal composition comprising a herbicidally effective amount of a hydroxyacetic acid amide derivative of the formula I and an agricultural adjuvant.

Further, the present invention provides a method for killing weeds, which comprises applying a herbicidally effective amount of a hydroxyacetic acid amide derivative of the formula I to a locus to be protected.

Now, the present invention will be described in detail with reference to the preferred embodiments.

The compound of the present invention may be prepared by various methods. Typical processes for the production are represented by the following formulas II and III, wherein R, $R_1$ and Hal are as defined above.

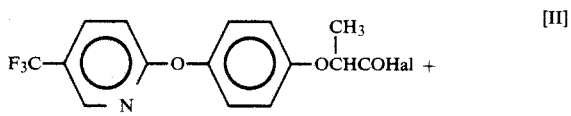

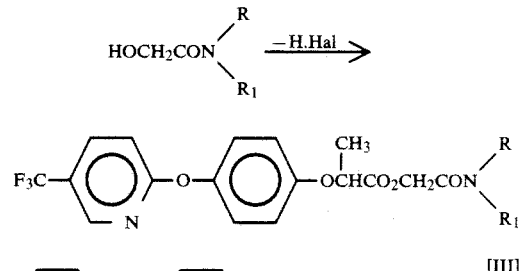

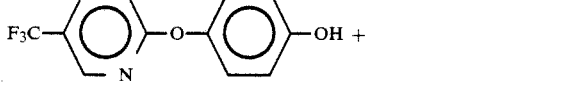

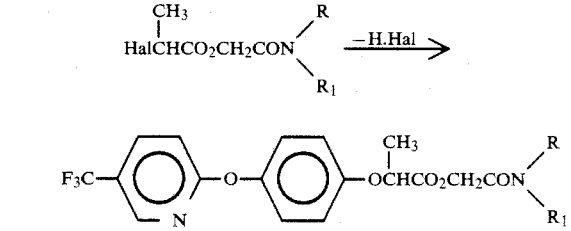

These reactions can be conducted in the presence or absence of a solvent by using a proper base, whereby the compound of the present invention is obtainable.

As the solvent for the reaction, a ketone such as acetone or methyl ethyl ketone, an aromatic hydrocarbon such as benzene, toluene or xylene, an ether such as ethyl ether, tetrahydrofuran or dioxane, a halogenated hydrocarbon such as chlorobenzene, chloroform, carbon tetrachloride or dichloroethane, a tertiary amine such as triethylamine, pyridine or dimethylaniline, or a polar solvent such as acetonitrile, dimethylformamide, dimethylsulfoxide or phosphoric acid hexamethyl triamide, may be employed.

As the base, a tertiary amine such as triethylamine, pyridine, 1,8-diazabicyclo-(5,4,0)-7-undecene or dimethylaniline, an alkali metal hydroxide such as sodium hydroxide or potassium hydroxide, an alkaline earth metal hydroxide such as calcium hydroxide, an alkali metal carbonate such as sodium carbonate, potassium carbonate, sodium hydrogencarbonate or potassium hydrogencarbonate, or a metal hydride such as sodium hydride, may be employed. The reactions proceed usually at a temperature of from about 0° C. to about 150° C., preferably from about 20° C. to about 100° C. The reaction time is usually from a few minutes to about 48 hours.

When the compound of the present invention is used as a herbicide, it may be formulated into a formulation such as an emulsifiable concentrate, a wettable powder, a dust or granules by incorporating various adjuvants such as a diluent, a solvent or a surfactant. In the herbicidal composition of the present invention, the compound of the formula I is incorporated as an active ingredient usually in an amount of from 0.1 to 90% by weight, preferably from 1 to 80% by weight.

In some cases, it is effective to incorporate as other herbicides as shown below for the purpose of reducing the labor for the application or for the purpose of expanding the range of the weeds to be effectively controlled.

2,4-dichlorophenoxy acetic acid, and its salts, esters and alkylamine salts,
2-methyl-4-chlorophenoxy acetic acid, and its salts and esters,
2-methyl-4-chlorophenoxy acetic acid, and its salts and esters,
d,l-2-(4-chloro-o-tolyloxy)propionic acid, and its salts and esters,
4-cyano-2,6-diiodophenyl octanoate,
2,4-dichlorophenyl-4'-nitrophenyl ether,
2,4,6-trichlorophenyl-4'-nitrophenyl ether,
2,4-dichlorophenyl-3'-methoxy-4'-nitrophenyl ether,
3,4-dichlorocarbanilide acid methyl,
3-chlorocarbanilide acid isopropyl,
diethylthiocarbamide acid-S-4-chlorobenzyl,
4-nitrophenyl-3',5'-xylyl ether,
hexahydro-1H-azepine-1-carbothio acid-S-ethyl,
3,4-dichloropropionanilide,
2-chloro-2',6'-diethyl-N-(butoxymethyl)acetoanilide,
2-chloro-2',6'-diethyl-N-(m-propoxyethyl)acetoanilide,
1-(α,α-diethylbenzyl)-3-p-tolyl urea,
2,4-bis(ethylamino)-6-methylthio-1,3,5-triazine,
2-ethylamino-4-isopropylamino-6-methylthio-1,3,5-triazine,
2,4-bis(isopropylamino)-6-methylthio-1,3,5-triazine,
5-tert-butyl-3-(2,4-dichloro-5-isopropoxyphenyl)-1,3,4-oxadiazoline-2-one,
2,6-dichlorobenzonitrile,
2,6-dichlorothiobenzamide,
2-amino-3-chloro-1,4-naphthoquinone,
2,4-dichlorophenyl-3'-carbomethoxy-4'-nitrophenyl ether,
N-p-chlorobenzyloxyphenyl-3,4,5,6-tetrahydrophthalimide,
2,4-dichlorophenyl-3'-ethoxyethoxy-4'-nitrophenyl ether,
N-(1-ethylpropyl)-2,6-dinitro-3,4-xylidine,
4-(2,4-dichlorobenzoyl)-1,3-dimethyl-pyrazol-5-yl-p-toluenesulfonate,
4-(2,4-dichlorobenzoyl)-1,3-dimethyl-5-(benzoylmethoxy)pyrazole,
4-(2,4-dichloro-3-methylbenzoyl)-1,3-dimethyl-5-(benzoylmethoxy)pyrazole,
4-(2,4-dichlorobenzoyl)-1-methyl-5-(benzoylmethoxy)-pyrazole,
O,O-diisopropyl-2-(benzsulfonamide)ethylene dithiophosphate,
3,3'-dimethyl-4-methoxybenzophenone,
α-(2-naphthoxy)propionanilide,
O-ethyl-O-(3-methyl-6-nitrophenyl)-N-sec-butylphosphorothioamidate,
3-isopropyl-2,1,3-benzothiadiazinon-(4)-2,2-dioxide and its salts,
S-(2-methyl-1-pyperidinyl-carbonylmethyl)-O,O-di-n-propyldithiophosphate,
S-benzyl-N,N-dimethylthiocarbamate.

It is possible to provide a mixed herbicide effective against may variety of weeds, by a combination of the compound of the present invention with one or more of the above herbicides.

When the compound of the present invention is applied, the dose is usually within a range of from 0.05 to 10 kg/ha, preferably from 0.1 to 5 kg/ha.

Now, the present invention will be described in further detail with reference to Examples. However, it should be understood that the present invention is by no means restricted to these specific Examples.

EXAMPLE 1

N-methyl-N-methoxyethyl-aminocarbonylmethyl 2-[4-(4-trifluoromethyl-2-pyridyloxy)phenoxy]propionate (Compound No. 3)

0.98 g of N-methyl-N-methoxyethyl-hydroxyacetic acid amide was dissolved in 30 ml of dichloromethane. To this solution, a solution of 2.12 g of 2-[4-(4-trifluoromethyl-2-pyridyloxy)phenoxy]propionic acid chloride in 10 ml of dichloromethane was dropwise added at room temperature. The mixture was stirred for 10 minutes at room temperature, and 0.64 g of triethylamine was added. The mixture was stirred at room temperature for 8 hours. Then, water was added to the reaction mixture, and the dichloromethane solution was separated, washed with water and dried over anhydrous magnesium sulfate. Then, the solvent was distilled off, and the residue was purified by column chromatography (silica gel, developed with benzene/ethyl acetate=10/1 (v/v) to obtain 1.68 g of the desired product ($n_D^{25}$: 1.5155).

Typical examples of the compound of the present invention are presented in Table 1, and the results of the elemental analyses thereof are shown in Table 2.

TABLE 1

$$F_3C-\underset{N}{\underset{||}{\bigcirc}}-O-\bigcirc-OCHCO_2CH_2CON\underset{R_1}{\overset{CH_3}{\underset{|}{<}}}\overset{R}{}$$

| Compound No. | R | $R_1$ | Physical properties |
|---|---|---|---|
| 1 | $CH_2-C\equiv CH$ | $CH_2-C\equiv CH$ | $n_D^{25}$ 1.5277 |
| 2 | $CH_2-CH=CH_2$ | $CH_2-CH=CH_2$ | $n_D^{25}$ 1.5277 |

TABLE 1-continued $$F_3C-\underset{N}{\underset{||}{\bigcirc}}-O-\bigcirc-OCHCO_2CH_2CON\underset{R_1}{\overset{R}{\diagup}}$$
with CH$_3$ on the OCH carbon

| Compound No. | R | R$_1$ | Physical properties |
|---|---|---|---|
| 3 | CH$_3$ | (CH$_2$)$_2$—OCH$_3$ | $n_D^{25}$ 1.5277 |

TABLE 2

Elemental analyses of the typical compounds of the present invention

| Compound No. | Molecular formula | Measured values (%) | Calculated values (%) |
|---|---|---|---|
| 1 | C$_{23}$H$_{19}$F$_3$N$_2$O$_4$ | C 62.12, H 4.27, N 6.51 | C 62.16, H 4.30, N 6.30 |
| 2 | C$_{23}$H$_{23}$F$_3$N$_2$O$_4$ | C 61.44, H 5.26, N 5.99 | C 61.60, H 5.16, N 6.24 |
| 3 | C$_{21}$H$_{23}$F$_3$N$_2$O$_5$ | C 57.15, H 5.15, N 6.00 | C 57.27, H 5.26, N 6.36 |

TABLE 3

| | Dose (g/a) | | | | | |
|---|---|---|---|---|---|---|
| | Barnyardgrass at germination | | | Barnyardgrass of 1.5 leaf stage | | |
| Compound No. | 10 | 2.5 | 0.6 | 40 | 10 | 2.5 |
| 1 | 5 | 5 | 5 | 5 | 5 | 5 |
| 2 | 5 | 5 | 5 | 5 | 5 | 5 |
| 3 | 5 | 5 | 4–5 | 5 | 5 | 5 |
| Non-treated area | 0 | 0 | 0 | 0 | 0 | 0 |

Now, specific formulations for the compounds of the present invention will be described. In these Examples, "parts" means "parts by weight".

EXAMPLE 2

Emulsifiable concentrate

20 Parts of Compound No. 2 of the present invention, 60 parts of xylene and 20 parts of Sorpol 2806B (tradename, Toho Kagaku Kogyo K.K.) were uniformly mixed and stirred to obtain an emulsifiable concentrate.

EXAMPLE 3

Wettable powder

A mixture comprising 78 parts of jeeklite, 17 parts of white carbon and 5 parts of Sorpol 5039 (tradename, manufactured by Toho Kagaku Kogyo K.K.), and Compound No. 3 of the present invention were mixed in a ratio of 4:1 to obtain a wettable powder.

Now, the herbicidal effects of the compounds of the present invention will be described with reference to specific Examples.

EXAMPLE 4

Herbicidal test against barnyardgrass

Paddy field soil was filled in a 1/5000 are Wagner pot, and paddled and leveled, and then 50 seeds of barnyardgrass were sown. The water level was maintained at a depth of 3 cm, and when the barnyardgrass was germinated and reached 1.5 leaf stage, the compound of the present invention was formulated into an emulsifiable concentrate in accordance with Example 2 and a predetermined amount thereof was diluted with water and uniformly applied on the water surface.

On the 15th day after the treatment with the herbicide, the herbicidal effects and the phytotoxicity were examined. The results are shown in Table 3. The herbicidal effects were evaluated in accordance with the following standards.

| Evaluation indices | Herbicidal effect |
|---|---|
| 5 | Complete kill |
| 4 | 80–99% control |
| 3 | 60–79% control |
| 2 | 40–59% control |
| 1 | 20–39% control |
| 0 | No effect |

EXAMPLE 5

Test for controlling barnyardgrass by direct sowing in flooded paddy field

Paddy field soil was filled in a 1/5000 are Wagner pot, and paddled and leveled, and then 20 seeds of paddy rice plants (variety: Nihonbare) and 50 seeds of barnyardgrass were sown. When the rice seeds and barnyard seeds germinated, the water level was maintained at a depth of 3 cm, and the compound of the present invention was formulated into an emulsifiable concentrate in accordance with Example 2 and a predetermined amount thereof was diluted with water and uniformly applied to the water surface.

On the 14th day after the treatment with the herbicide, the herbicidal effects and the phytotoxicity were examined. The results are shown in Table 4.

TABLE 4

| Compound No. | Plant and weed | Dose of active ingredient (g/a) | |
|---|---|---|---|
| | | 2.5 | 0.6 |
| 1 | rice | 100 | 100 |
| | barnyardgrass | 0 | 0 |
| 2 | rice | 92 | 100 |
| | barnyardgrass | 0 | 0 |
| 3 | rice | 100 | 100 |
| | barnyardgrass | 0 | 5 |
| Non-treated area | rice | 100 | 100 |
| | barnyardgrass | 100 | 100 |

The numerical values indicate the weights of living plants.

EXAMPLE 6

Foliage treatment test

Soil was put into a 1/5000 are Wagner pot and leveled to simulate an upland field. Predetermined amounts of seeds of barnyardgrass, oat, radish and soybean were sown, and covered with a soil containing many seeds of gramineous weeds such as crabgrass (*Digitaria sanguinalis*), greenfoxtail (*Setaria viridis*) and barnyardgrass (*Echinochloa crus-galli*) in a thickness of about 1 cm, and cultured under a condition suitable for growth.

When the weeds reached 3–3.5 leaf stage, a herbicide having a predetermined concentration was sprayed uniformly to the foliage. On the 10th day after the treatment, the states of growth of weeds and plants were examined. The results as shown in Table 5 were obtained. The evaluation standards were the same as in Example 4.

TABLE 5

| Compound No. | Concentration of active ingredient (ppm) | Growth controlling degree | | | | |
|---|---|---|---|---|---|---|
| | | Rap | Gly | Ech | Ave | Gramineous weeds |
| 1 | 500 | 0 | 0 | 5 | 5 | 5 |
| | 250 | 0 | 0 | 5 | 5 | 5 |
| 2 | 500 | 0 | 0 | 5 | 5 | 5 |
| | 250 | 0 | 0 | 5 | 5 | 5 |
| 3 | 500 | 0 | 0 | 5 | 5 | 5 |
| | 250 | 0 | 0 | 5 | 5 | 5 |
| Non-treated | — | 0 | 0 | 0 | 0 | 0 |
| area | — | 0 | 0 | 0 | 0 | 0 |

Rap: radish (*Raphanus raphanistrum*)
Gly: soybean (*Glycine max*)
Ech: barnyardgrass (*Echinochloa crus-galli*)
Ave: oat (*Ave sative*)

The compound of the present invention exhibits strong herbicidal effects against barnyardgrass which is one of the strongest weeds, by the application to the water surface in the cultivation of rice plants, while giving no substantial effects against rice plants, and also exhibits selective herbicidal effects in the cultivation of broad leaf crop plants such that it is capable of controlling gramineous weeds without adversely affecting the crop plants.

We claim:

1. A hydroxyacetic acid amide derivative having the formula:

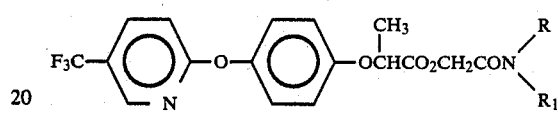

(I)

wherein each of R and $R_1$ which may be the same or different, is an alkyl, alkenyl, alkynyl or alkoxyalkyl group having from 1 to 4 carbon atoms, provided that R and $R_1$ are not simultaneously alkyl groups.

2. The compound of the formula I according to claim 1, wherein each of R and $R_1$ is $-CH_2-C\equiv CH$.

3. The compound of the formula I according to claim 1, wherein each of R and $R_1$ is $-CH_2-CH=CH_2$.

4. The compound of the formula I according to claim 1, wherein R is $CH_3$ and $R_1$ is $-(CH_2)_2-OCH_3$.

5. A herbicidal composition comprising a herbicidally effective amount of a hydroxyacetic acid amide derivative of the formula I as defined in claim 1 and an agricultural adjuvant.

6. A method for killing weeds, which comprises applying a herbicidally effective amount of a hydroxyacetic acid amide derivative of the formula I as defined in claim 1 to a locus to be protected.

* * * * *